Figure 2C:
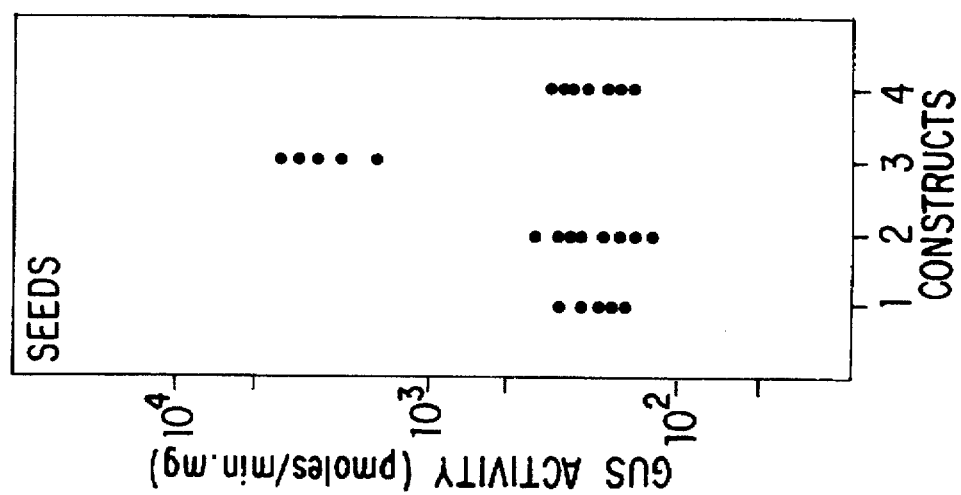

United States Patent [19]

Chua

US005723751A

[11] Patent Number: 5,723,751
[45] Date of Patent: Mar. 3, 1998

[54] EXPRESSION MOTIFS THAT CONFER TISSUE AND DEVELOPMENT-SPECIFIC EXPRESSION IN PLANTS

[75] Inventor: Nam-Hai Chua, Scarsdale, N.Y.

[73] Assignee: The Trustees of Rockefeller University, New York, N.Y.

[21] Appl. No.: 378,986

[22] Filed: Jan. 24, 1995

Related U.S. Application Data

[63] Continuation of Ser. No. 982,792, Nov. 30, 1992, abandoned.

[51] Int. Cl.[6] .............. A01H 5/00; C12N 15/29; C12N 5/04; C12N 15/82
[52] U.S. Cl. ............ 800/205; 536/24.1; 536/23.2; 435/172.3; 435/240.4
[58] Field of Search ............. 536/24.1, 23.2; 435/172.3; 800/205

[56] References Cited

U.S. PATENT DOCUMENTS 5,097,025  3/1992  Benfey et al. ............ 536/24.1

OTHER PUBLICATIONS

Benfey et al., 1990, Embo J. 9:1667–1684.
Benfey and Chua, 1990, Science 250:959–966.
DeLisle and Ferl, 1990, Plant Cell 2:547–557.
Giuliano et al., 1988, Proc. Natl. Acad. Sci. USA 85:7089–7093.
Guiltinan et al., 1990, Science 250:267–271.
Johnson and McKnight, 1989, Annual Rev. Biochem. 58:799–839.
Marcotte et al., 1989, Plant Cell 1:969–976.
Mundy et al., 1990, Proc. Natl. Acad. Sci USA 87:1406–1410.
Oeda et al., 1991, Embo J. 10:1793–1802.
Salinas et al., 1992, Plant Cell 4:1485–1493.
Schindler et al., 1992, Embo J. 11:1261–1273.
Schultze–Lefert et al., 1989, Embo. J. 8:651–656.
Skriver et al., 1991, Proc. Natl. Acad. Sci USA 88:7266–7270.
Staiger et al., 1991, Eur. J. Biochem. 199:519–527.
Tabata et al., 1989, Science 245:965–967.
Weisshaar et al., 1991, Embo J. 10:1777–1786.
Williams et al., 1992, Embo J. 11:1261–1273.
Waison et al. (eds), Molecular Biology of the Gene, 4th ed. Benjamin/Cummings Publishing Co., Menlo Park, CA, p. 313 (1987).

*Primary Examiner*—David T. Fox
*Assistant Examiner*—Thomas Haas
*Attorney, Agent, or Firm*—Pennie & Edmonds

[57] ABSTRACT

The present invention relates to the use of DNA sequence motifs to regulate gene expression in a tissue- or developmental-specific manner in transgenic plants. The invention generally relates to the engineering and use of G-box related sequence motifs, specifically Iwt and PA motifs, which function as cis-elements of promoters, to regulate the expression of heterologous genes in transgenic plants. PA enhances high level expression in roots, low level expression in leaves and little or no expression in seeds. By contrast, Iwt confers preferential expression in seeds, but in a developmentally-regulated manner.

11 Claims, 10 Drawing Sheets

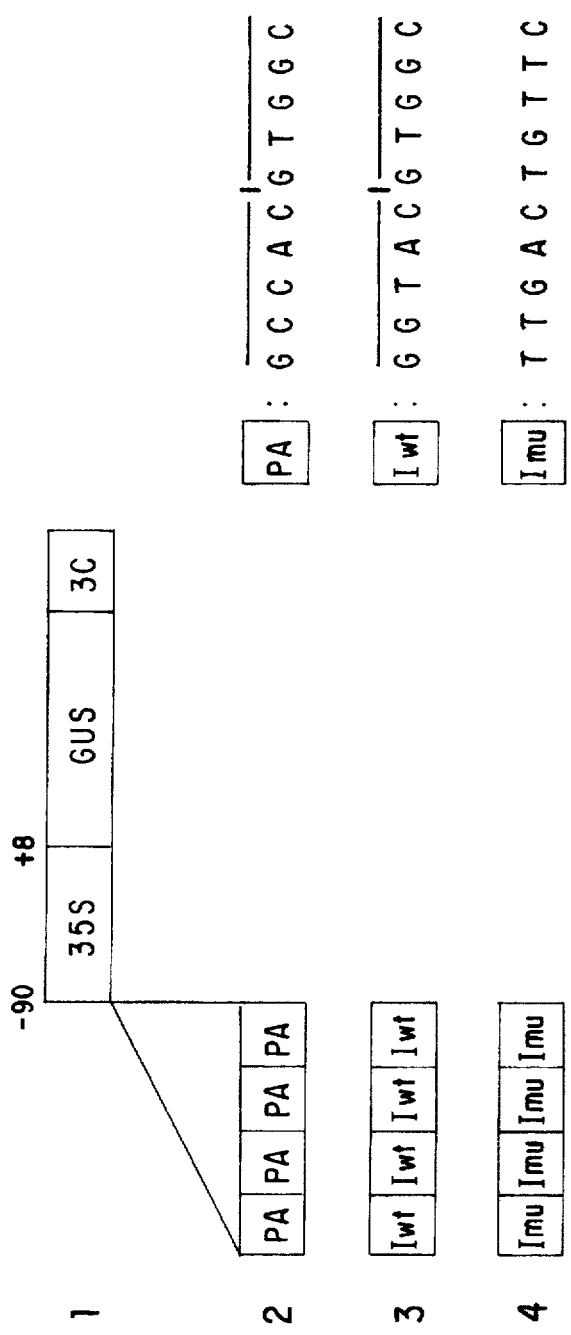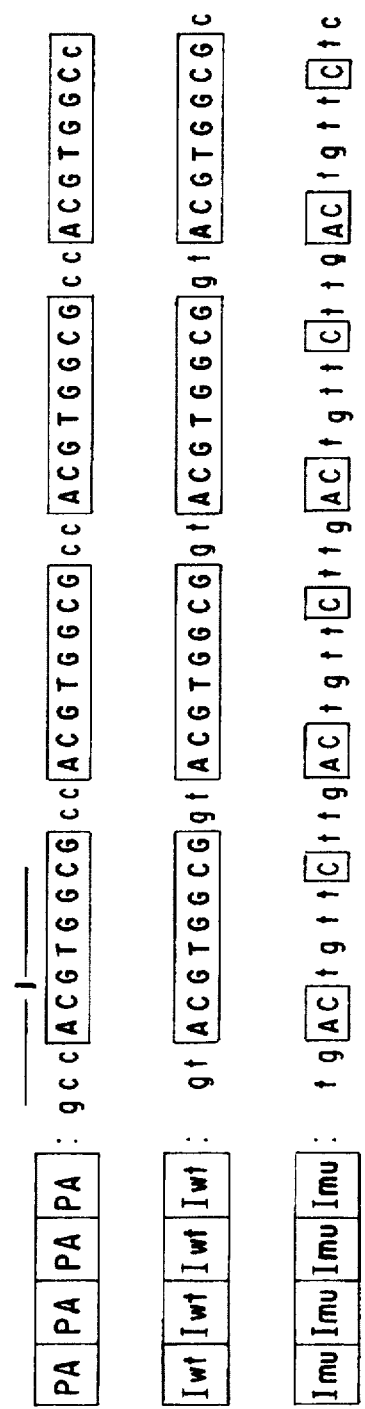
FIG.1A
FIG.1B

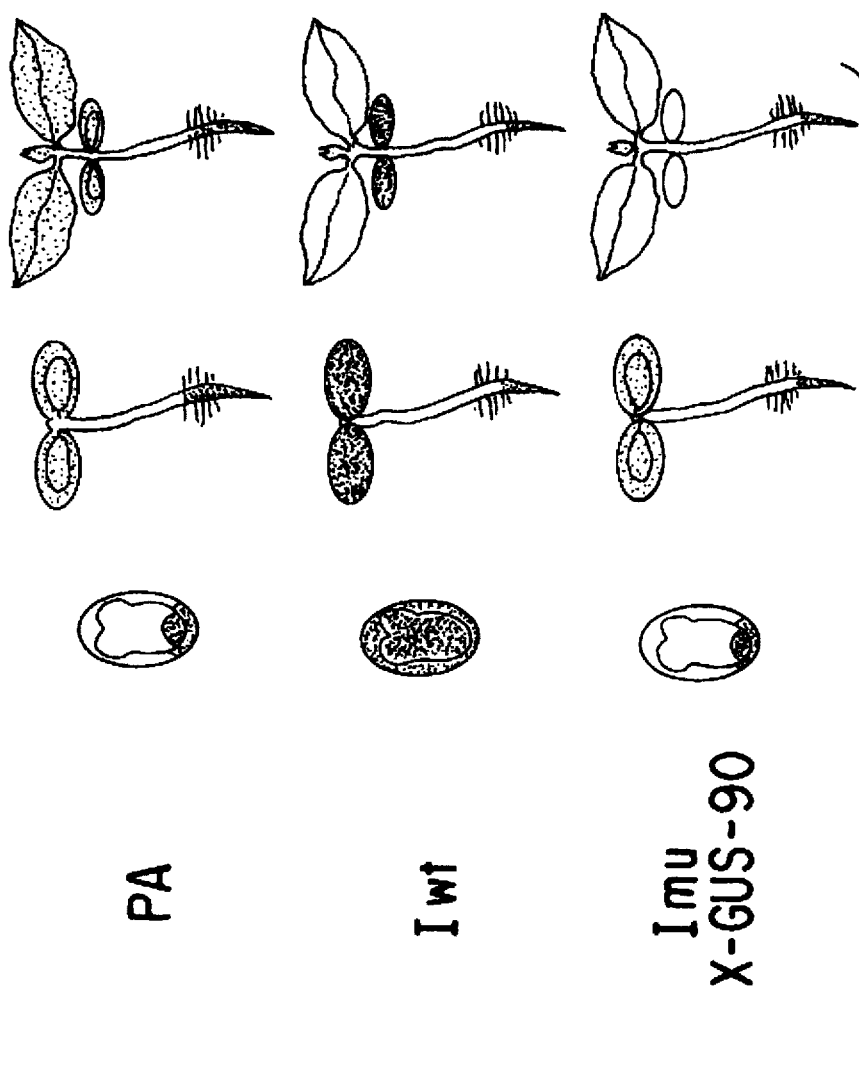

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: unknown ( i i ) MOLECULE TYPE: G-box element sequence ( x i ) SEQUENCE DESCRIPTION: SEQ ID NO:1:

MACACGTGGC A                    1 1

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:2:

GTACGTGGCG                    1 0

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:3:

GCCACGTGGC                    1 0

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif related sequence ( x i ) SEQUENCE DESCRIPTION: SEQ ID NO:4:

TGACTGTTCT                    1 0

( 2 ) INFORMATION FOR SEQ ID NO:5:

```
( i ) SEQUENCE CHARACTERISTICS:
    ( A ) LENGTH: 11 base pairs
    ( B ) TYPE: nucleic acid
    ( C ) STRANDEDNESS: double
    ( D ) TOPOLOGY: unknown ( i i ) MOLECULE TYPE: Hex-motif related sequence ( x i ) SEQUENCE DESCRIPTION: SEQ ID NO:5:

GGACGCGTGG C                              1 1

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: Opaque 2 binding site ( x i ) SEQUENCE DESCRIPTION: SEQ ID NO:6:

TCTACGTGGA                                1 0
```

EXPRESSION MOTIFS THAT CONFER TISSUE AND DEVELOPMENT-SPECIFIC EXPRESSION IN PLANTS

This is a continuation of application Ser. No. 07/982,792, filed Nov. 30, 1992, now abandoned.

TABLE OF CONTENTS

1. Introduction
2. Background Of The Invention
   2.1 Manipulation Of Plant Promoters
   2.2 G-Box Elements
   2.3 TAF-1 Transactivating Factor
3. Summary Of Invention
   3.1 Definitions
4. Description Of The Figures
5. Detailed Description Of The Invention
   5.1 PA and Iwt Motifs
   5.2 PA or Iwt Motif Modified Promoters
   5.3 Engineering A Gene Of Interest Controlled By The Modified Promoters
   5.4 Production Of Transgenic Plants And Plant Cells
   5.5 Expression Of Target Gene Products In Transgenic Plants
6. Example: Tissue-Specific And Developmentally Regulated Expression Of Target Gene Products In Transgenic Tobacco
   6.1 Materials And Methods
      6.1.1 G-Box-Related Constructs
      6.1.2 Transgenic Plants
      6.1.3 Histochemical Staining
      6.1.4 Gus Enzyme Assays
      6.1.5 Northern Analysis
   6.2 Results
      6.2.1 Engineered Transgenic Plants
      6.2.2 Expression Of Target Gene Product In Mature Plants
      6.2.3 Expression Of Target Gene Produced During Seed Development
      6.2.4 Expression Of Target Gene Product In Young Seedlings
      6.2.5 Expression Pattern Of TAF-1 mRNA

1. INTRODUCTION

The present invention relates to the use of two G-box related nucleotide sequences to direct tissue-specific and developmentally-regulated gene expression of target gene products in transgenic plants.

2. BACKGROUND OF THE INVENTION

One of the important challenges in genetic engineering of plants is constructing novel promoters that have precisely tailored tissue-specific or developmentally-regulated activities. The availability of tailored promoters would enable the expression of engineered traits in only the desired tissue or organ locations, or in particular developmental stages. Such exact control of transgene expression is highly desirable to enhance the biological efficiency and performance predictability of trangenic plants. However, attempts to engineer such systems have been met with limited success.

2.1 Manipulation of Plant Promoters

Plant RNA polymerase II promoters, like those of other higher eukaryotes, have complex structures and are comprised of several distinct elements. One essential element is the TATA box. It determines the transcription initiation site and is typically located −35 to −25 basepairs (bp) upstream of the initiation site, which is defined as position +1 (Breathnack and Chambon, 1981, Ann Rev. Biochem. 50: 349–383; Messing et al., 1983, In: *Genetic Engineering of Plants*, Kosuge, Meredith and Hollaender, (eds.), pp. 211–227). Another common element is located between −70 and −100 bp upstream and has the consensus sequence CCAAT. In plants, the CCAAT box may have a different consensus sequence and has been termed the AGGA box. (Messing et al. ibid). Besides TATA and CCAAT boxes, virtually all eukaryotic promoters studied to date contain additional upstream DNA sequences that regulate promoter activity (Benoist and Chambon, 1981, Nature 290: 304–310; Gruss et al., 1981, Proc. Nat. Acad. Sci USA 78: 943–947; Khoury and Gruss, 1983, Cell 27: 313–314.) These upstream regulatory sequences are variously known as enhancers or upstream activating sequences. Such sequences are variable in length and may extend from around −100 bp to 1,000 bp or more 5' upstream of the transcription initiation site.

Early attempts in developing novel plant promoters involved recombining regulatory sequences of one promoter with parts of another promoter (Fluhr et al., 1986, Science 232: 1106–1112; Ellis et al., 1987, EMBO J. 6: 11–16). Such constructs involved adding a heterologous regulatory sequence to an active promoter with its own partial or complete regulatory sequences (Ellis et al., id.; Strittmatter and Chua, 1987, Proc. Nat. Acad. Sci. USA 84: 8986–8990; Poulsen and Chua, 1988, Mol. Gen. Genet. 214: 16–23; Comai et al., 1991, Plant Molec. Biol. 15: 373–381). Alternatively, modified promoters have also been developed by adding a heterologous regulatory sequence to the 5' upstream region of an inactive, truncated promoter, i.e. a promoter that spans only the core TATA and, sometimes, the CCAAT elements, (Fluhr et al., 1986, ibid; Strittmatter and Chua, 1987, Proc. Nat. Acad. Sci. USA 84: 8986–8990; Aryan et al., 1991, Mol. Gen. Genet. 225: 65–71). While such recombinations can produce promoters with novel activities, they generally have not been particularly useful in producing tailored promoters with precisely controlled or limited activities. That is because most the known regulatory sequences conferred manifold complex tissue-, developmental- or environmental activities.

Dissection of plant regulatory sequences have shown that they are typically comprised multiple distinct "cis-elements" each appearing to confer a different segment of the original spectrum of activity (See Strittmatter and Chua, ibid; Ellis et al., ibid; Benfey et al., 1990, EMBO J 9: 1677–1684). The molecular basis of such activity seemed to reside in a cis-element's ability to bind trans-acting protein factors that regulate transcription initiation. Some cis-elements may bind with more than one factor, and these factors, in turn, may interact with different affinities with more than one cis-element (Johnson, P. F. and McKnight, S. L., 1989, Ann. Rev. Biochem. 58: 799–839). Despite the appreciation of cis-element's role in regulating transcription, no general understanding has emerged on what exactly comprises a cis-element or how cis-elements can be used, in isolated forms, to modify active promoters or construct novel promoters.

2.2 G-Box Elements

In plants, the G-box element or sequence motif exemplifies the promiscuity of certain DNA sequences in their interaction with multiple binding proteins. This element was first identified as an 11 bp sequence (5' C/A-

ACACGTGGCA 3') (SEQ. ID NO:1) located upstream of many genes encoding the small subunit of ribulose biphosphate carboxylase (Giuliano et al., 1988, Proc. Natl. Acad. Sci. USA 85: 7089–7093). Since then, cis-elements comprised of G-box or related sequence motifs with the CACGTG hexanucleotide core have been identified in the promoters of a diverse set of unrelated genes, including those controlled by visible and ultraviolet light (Schulze-Lefert et al., 1989, EMBO J. 8: 651–656), abscisic acid (ABA) (Guiltinan et al., 1990, Science 250: 267–271), wounding (Rosahl et al., 1986, Mol. Gen. Genet. 203: 214–220) or, anaerobiosis (DeLisle & Ferl, 1990, Plant Cell 2: 547–557. Recent data indicate that plant nuclear extracts contain a number of binding activities with specificity for G-box and related sequences (Staiger et al., 1991, Eur. J. Biochem. 199: 519–527; Williams et al., 1992, Plant Cell 4: 485–496). Indeed, several cDNA clones encoding proteins that specifically interact with cis-elements containing the CACGTG core have been isolated: wheat EmBP-1 (Guiltinan et al., 1990, Science 250: 267–271), wheat HBP-1a (Tabata et al., 1991, EMBO J. 10: 1459–1467), tobacco TAF-1 (Oeda et al., 1991, EMBO J. 10: 1793–1802), parsley CPRF-1, 2, 3 (Weisshaar et al., 1991, EMBO J. 10: 1777–1786, and Arabidopsis GBF-1, 2, 3 (Schindler et al., 1992, EMBO J. 11: 1261–1273). Interestingly, all these proteins belong to the bZIP class of transcription factors, i.e., they possess a basic domain abutting a leucine repeat. It has been shown that bZIP proteins bind as dimers to their target sites (cf. Johnson & McKnight, 1989, Annu. Rev. Biochem. 58: 799–839).

2.3 TAF-1 Transactivating Factor

The TAF-1 cDNA clone was isolated from a tobacco cDNA expression library by screening for proteins that show affinity for motif I (Iwt, 5' GTACGTGGCG 3') (SEQ. ID NO:2), a conserved sequence found in promoters of different ABA-responsive genes (see Skriver & Mundy, 1990, Plant Cell 2: 503–512 for a review). Because TAF-1 is a bZIP protein and because Iwt contains a G-box related core sequence TACGTG, the question arose whether the preferred binding site of TAF-1 might be the perfect palindrome PA, 5' GCCACGTGGC 3' (SEQ. ID NO:3) which contains the G-box hexameric core sequence CACGTG. Experiments showed that, indeed, TAF-1 binds to PA with a higher affinity (about 70 times) than to Iwt (Oeda et al., 1991, EMBO J. 10: 1793–1802).

The finding that TAF-1 can bind in vitro to two related sequence motifs, PA and Iwt, although with different affinities, poses interesting questions regarding binding and transcription activation in vivo. Transient expression of the TAF-1 gene in tobacco leaves showed that the factor is capable of activating the expression of Iwt motif containing promoters. Further, Northern blot analysis demonstrated that TAF-1 was highly expressed in roots but poorly expressed in leaves and stems (Oeda et al., 1991, EMBO J. 10: 1793–1802). Thus, in the simplest case, if both motifs interact with TAF-1 in vivo, then they should confer an expression pattern similar to that exhibited by TAF-1 expression; however, their activities in the expressing tissues may differ quantitatively, reflecting in some way their different binding affinity for the factor. Alternatively, if the motifs interact with different factors in vivo, then different expression profiles would be expected. Other more complicated scenarios are also possible.

The potential roles of Iwt and PA motifs in regulating gene expression remain to be determined. The presence of Iwt sequences as G-box related motifs in the 5' upstream regions of many plant promoters suggests that the Iwt motif might function as a cis-element in regulating transcription. A possible cis-element role for the PA motif is less apparent, since PA is an artificial derivative of the Iwt motif and is not known to be present in the regulatory regions of plant genes. Further, although TAF-1 activates Iwt motif containing promoters, it is not known what other transcriptional factors activate promoters that contain either the Iwt or PA motif.

3. SUMMARY OF INVENTION

The present invention relates to the use of DNA sequence motifs to regulate gene expression in a tissue- or developmental-specific manner in transgenic plants. The invention generally relates to the engineering and use of G-box related sequence motifs, specifically Iwt and PA motifs, which function as cis-elements of promoters, to regulate the expression of heterologous genes in transgenic plants. PA enhances high level expression in roots, low level expression in leaves and little or no expression in seeds. By contrast, Iwt confers preferential expression in seeds, but in a developmentally-regulated manner.

In accordance with the present invention, the Iwt or PA motif may be used in monomeric or various multimeric forms to modify promoters. Further, each motif may also be used singly or multiply, and in combinations with other motifs, to produce novel cis-elements with a specifically tailored spectrum of tissue- or developmental-specificities.

Promoters modified with Iwt or PA motif have a variety of uses, including, but not limited to, expressing or overexpressing proteins, anti-sense RNAs, and ribozymes in plant cell expression systems, in plant cultures, or in stably transformed plants. The gene expression under control of such modified promoters may be induced by hormone treatments, developmental processes, or differentiation processes.

The use of the PA- or Iwt-motif modified promoters may have particular value in engineering agronomically important plants. Such recombinant promoters would enable precise control of phenotypic traits in engineered plants and may be beneficially used to produce transgenic plants that have enhanced nutritional value; that have modified differentiation and development programs; or are resistant to a variety of factors including pests, pathogens, adverse environmental conditions or chemicals.

The invention is based, in part, on the surprising finding that the closely related Iwt and PA motifs, which differ in only two out of ten base-pairs, confer dramatically different tissue- and developmental-specificities to the promoters they modify. Iwt tetramers confer embryo-specific expression, whereas PA tetramers confer high level root expression, low level leaf expression, and no seed expression. The invention is illustrated herein by way of working examples in which the GUS reporter gene driven by Iwt- or PA-modified promoters were engineered into transgenic tobacco plants. GUS activity in different tissues and at different stages of plant development was analyzed quantitatively and qualitatively. The expression pattern of TAF-1 mRNA in different tissues of tobacco plants was also analyzed. These results demonstate that Iwt promotes expression in developing and mature seeds whereas PA confers preferential expression in roots. The results also demonstrate that TAF-1 mRNA is not expressed in seeds, although it is highly expressed in roots. On the basis of the foregoing results, interactions of TAF-1 with PA and Iwt sequences for regulating gene expression are proposed.

3.1 Definitions

The terms listed below, as used herein, will have the meaning indicated.

CaMV=Cauliflower Mosaic Virus
cDNA=complementary DNA
DAF=days after fertilization
DNA=deoxyribonucleic acid
GUS=1,3 β-Glucuronidase
MU=5' TGACTGTTCT 3' (SEQ. ID NO:4)
PA=5' GCCACGTGGC 3' (SEQ. ID NO:3)
PCR=polymerase chain reaction
PEG=polyethylene glycol
polyA=polyadenylated
rbcS=ribulose bisphosphate carboxylase small subunit
RNA=ribonucleic acid
Iwt=5' GTACGTGGCG 3' (SEQ. ID NO:2)

4. DESCRIPTION OF THE FIGURES

FIGS. 1A–1B. A schematic diagram of the constructs containing the perfect palindromic sequence (PA) (SEQ. ID NO:3), motif I wild type (Iwt) (SEQ. ID NO:2) and motif I mutant (Imu) (SEQ. ID NO:4). Oligonucleotides containing head-to-tail tetramer of PA, Iwt, and Imu were ligated to the −90 35S promoter in X-GUS-90 vector (construct 1) to produce constructs 2, 3, and 4, respectively. The vector X-GUS-90 contains the A domain (−90 to +8) from the CaMV 35S promoter, the −90 35S promoter, ligated to the GUS coding sequence with a 3' fragment of the pea rbcS-3C gene (Benfey & Chua, 1989, Science 244: 174–181). Tetramers were ligated to the vector, 5' to the A domain. FIG. 1A: Nucleotide sequences of PA, Iwt and Imu. FIG. 1B: Nucleotide sequences of PA, Iwt and Imu in tetrameric arrangement. Frames indicate bases shared by the three tetrameric motif sequences.

Figure 2B:
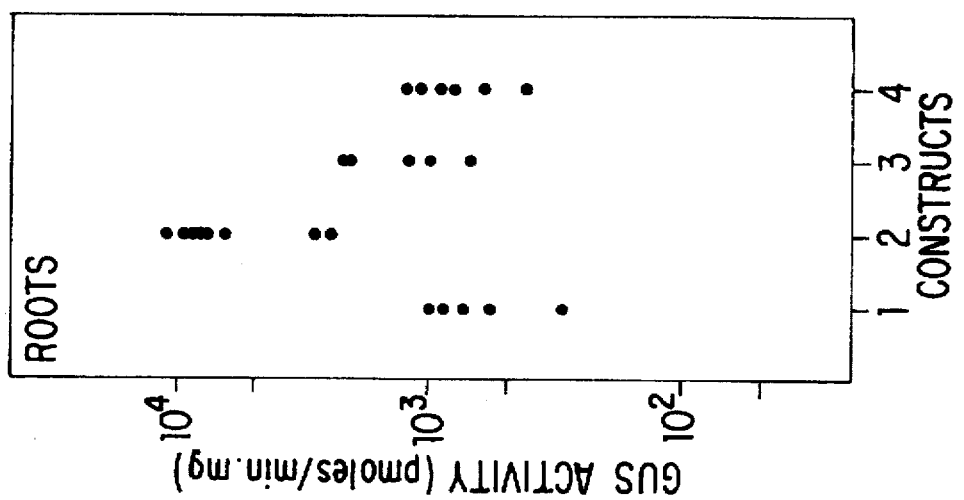
Figure 2A:
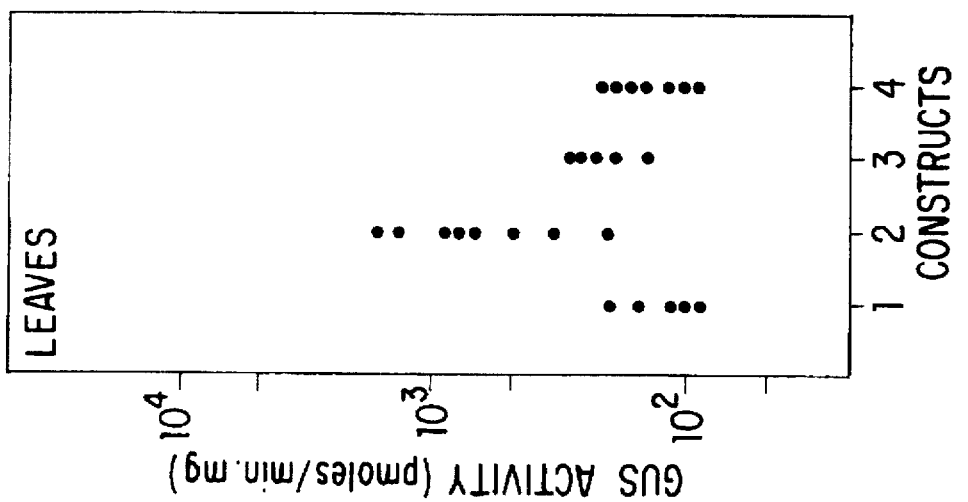

FIGS. 2A–2C. GUS activities of transgenic tobacco plants carrying the various chimeric constructs. Chimeric constructs were as described in FIGS. 1A–1B. GUS activities were measured as described in Material and Methods. Data from seven to ten independent transgenic plants for each construct are shown; the highest and the lowest values were not represented. Activity, represented in logarithmic scale, is expressed as picomoles of 4-methylumbelliferone produced per minute per milligram of protein. Each dot represents the activity of an independent transgenic line. FIG. 2A: Leaves from 7–10 week-old plants grown in a greenhouse, and from 7 week-old plants grown on supplemented MS medium. FIG. 2B: Roots from 7 week-old plants grown on supplemented MS media. FIG. 2C: Mature seeds.

Figure 3A:
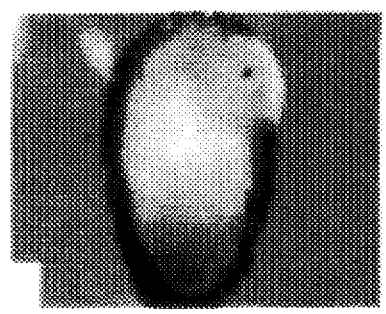
Figure 3B:
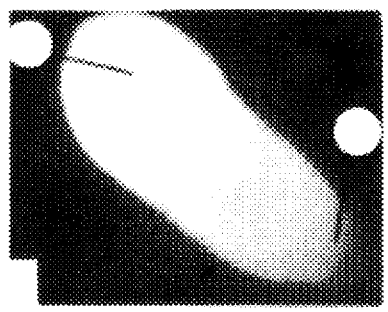
Figure 3C:
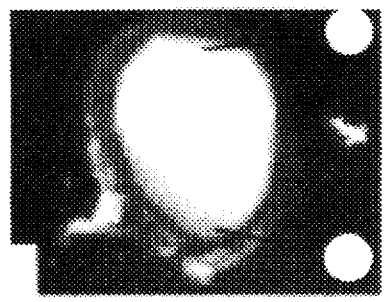
Figure 3D:
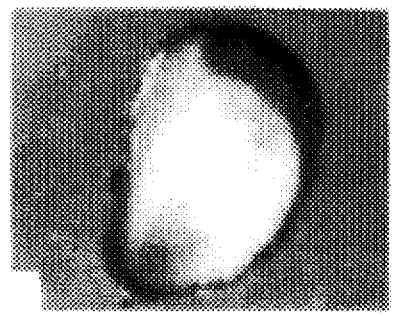
Figure 3E:
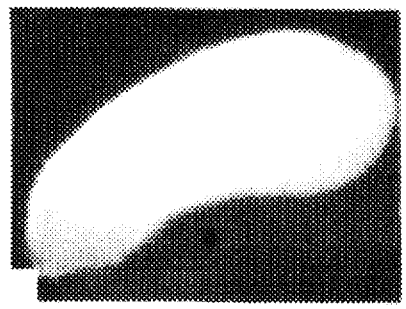
Figure 3F:
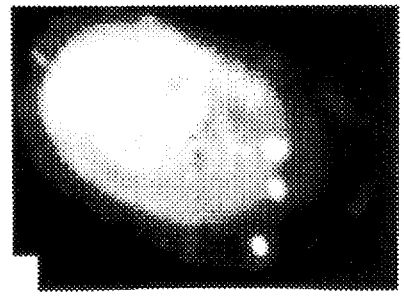
Figure 3G:
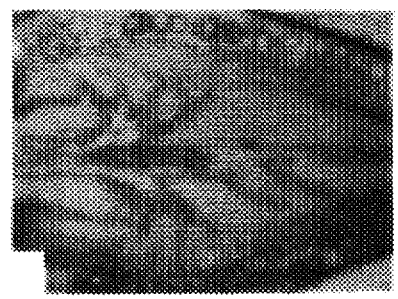
Figure 3H:
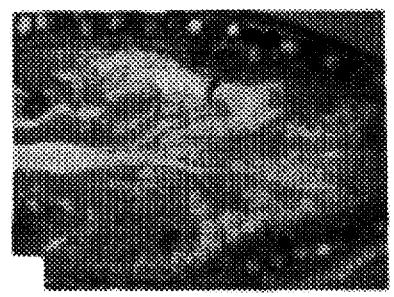
Figure 3I:
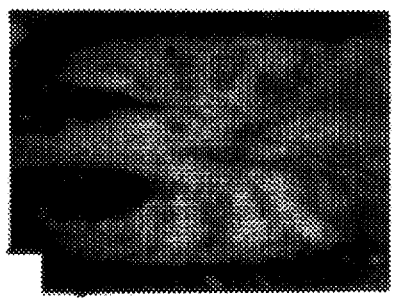
Figure 3J:
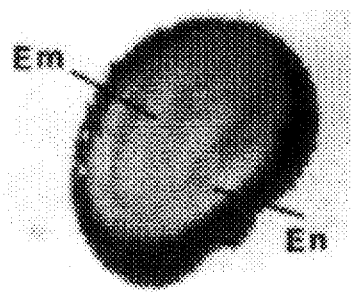
Figure 3K:
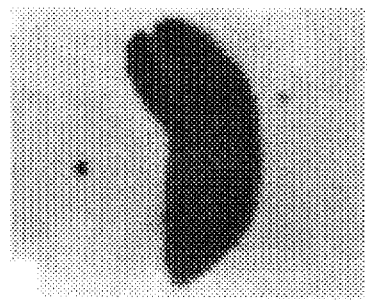
Figure 3L:
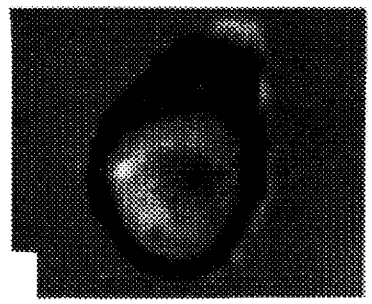

FIGS. 3A–3L. Histochemical localization of GUS expression in seeds from representative transgenic plants containing PA, Iwt, and Imu sequences. FIGS. 3A–3C: Mature seeds containing PA. Similar results were obtained with mature seeds containing Imu tetramers. FIGS. 3D–3F Mature seeds containing the X-GUS-90 vector. FIGS. 3G–3I: capsules of seeds containing Iwt tetramers at 10, 15, and 20 DAF, respectively. FIGS. 3J–3L: Mature seeds containing Iwt tetramers. FIGS. 3A, 3D, and 3J: Whole seeds. FIGS. 3B, 3E, and 3K: Embryos. FIGS. 3C, 3F, and 3L: Endosperms. C, cotyledon; En, endosperm; Em, embryo; Ra, radicle; Rp, radicle pole of endosperm; Cp, cotyledon pole of endosperm. Arrows in FIGS. 3H and 3I indicate GUS activity detected in developing seeds.

Figure 4A:
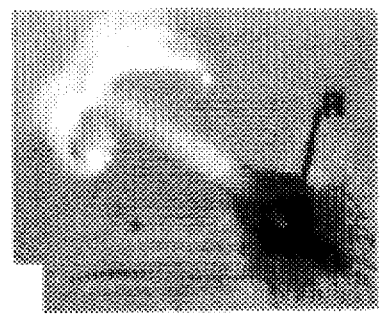
Figure 4B:
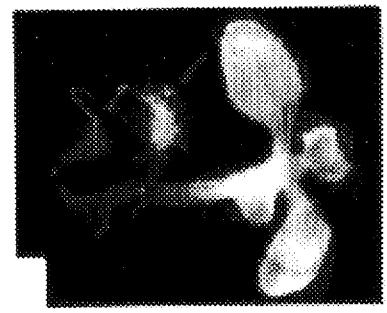
Figure 4C:
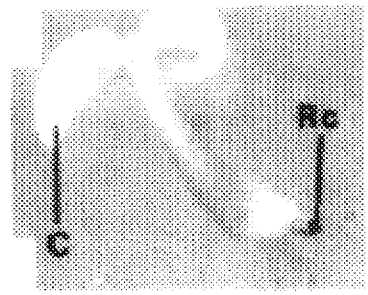
Figure 4D:
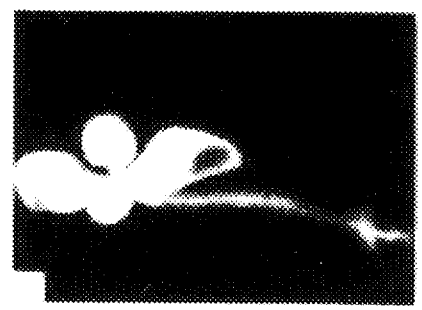
Figure 4E:
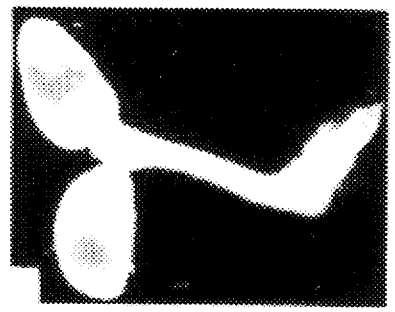
Figure 4F:

FIGS. 4A–4F. Histochemical localization of GUS expression in seedlings from representative transgenic plants containing PA, Iwt, and Imu sequences. FIGS. 4A–4B: Seedlings containing PA tetramers. FIGS. 4C–4D: Seedlings containing Imu tetramers. Similar results were obtained with seedlings containing the X-GUS-90 vector alone. FIGS. 4E–4F: Seedlings containing Iwt tetramers. FIGS. 4A, 4C, and 4E: Seven day-old seedlings. FIGS. 4B, 4D, and 4F: Fifteen day-old seedlings. C, cotyledon; R, root; Rc, root cap; L, first leaves.

Figure 5A:
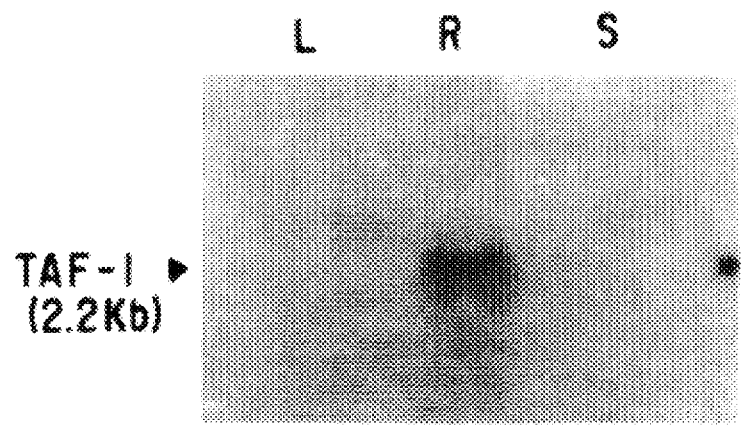
Figure 5B:
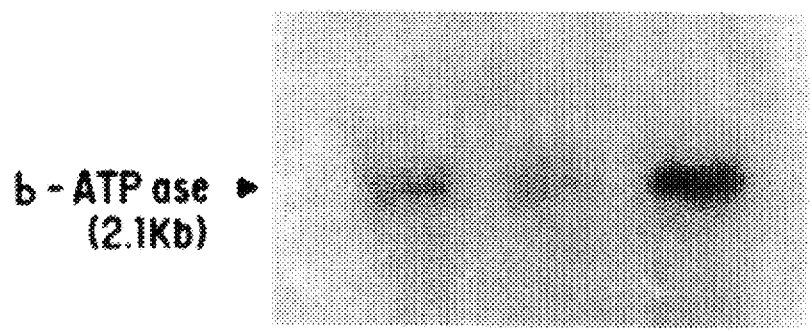

FIGS. 5A–5B. Expression of TAF-1 mRNA in different organs of tobacco plant. One μg of polyA-plus RNA from leaves (L), roots (R), and 20 DAF seeds (S), was used. The hybridization probes were TAF-1 cDNA (FIG. 5A) and β-ATPase cDNA (FIG. 5B). See Material and Methods for more details.

FIG. 6. Schematic representation of expression patterns conferred by PA, Iwt, and Imu sequences in seeds and seedlings. Top panel, expression pattern conferred by the PA sequence; Middle panel, expression pattern conferred by the Iwt sequence; Bottom panel, expression pattern conferred by the Imu sequence and by the vector X-GUS-90. Expression patterns of (from left to right) seeds, 7 day-old seedlings and 15 day-old seedlings are shown. High level expression is indicated by darkened areas, whereas crosshatching indicates low levels of expression.

5. DETAILED DESCRIPTION OF THE INVENTION

The present invention relates to the use of two closely related DNA sequence motifs that confer very different developmental- and tissue-specific expression patterns on plant promoters. The invention is illustrated by working examples involving the design of transgenic tobacco plants containing recombinant DNA sequences comprised of tetramers of Iwt or PA sequence motifs regulating the expression of a truncated promoter (−90 35S promoter). The perfect palindromic PA motif conferred on the chimeric gene construct high level expression in roots and low level expression in leaves and no expression in seeds. In contrast, the wild type Iwt motif conferred on the chimeric gene construct developmental-specific expression in seed tissues.

5.1 PA and Iwt Motifs

PA (SEQ. ID NO:3) and Iwt (SEQ. ID NO:2) motifs and multimers of these motifs, described in FIG. 1, may be obtained by chemical synthesis or by cloning from recombinant DNA constructs or appropriate cellular source containing such motifs or multimers. For example, chemical synthesis methods well known to those skilled in the art can be used to synthesize the motifs and their multimers reported in FIG. 1. See, for example, Caruthers et al., 1980, Nuc. Acids Res. Symp. Ser. 7: 215–233; Chow and Kempe, 1981, Nuc. Acids Res. 9: 2807–2817. These sequences may be synthesized with additional flanking sequences that contain appropriate and useful restriction enzyme sites for facilitating subsequent manipulations of these motifs containing sequences.

Alternatively, synthetic DNA sequences that are partially or wholly homologous to the desired motif or multimer may be used as hybridization probes in cloning DNA fragments containing such motifs or multimers from appropriate genomic sources. The cloned fragments are then mapped and sequenced to pin-point the locations of the motif-containing sequences. Smaller fragments containing such sequences are then subcloned and further modified as desired. The recombinant DNA methods for doing all of the aforementioned steps of isolation, characterization, and manipulation are well known to those skilled in the art and may be found in reference sources such as Sambrook et al., 1989, *Molecular Cloning, A Laboratory Manual*, Cold Spring Harbor Laboratory Press, Plainview, N.Y.

Alternatively, synthetic DNA sequences that are partially or wholly homologous to the desired motif or multimer may also be used as primers in polymerase chain reactions (PCR) to amplify and isolate motif-containing sequences from any appropriate DNA source. This approach may also be used to modify such motif-containing sequences before amplification and isolation, or to construct the desired motif-containing sequence de novo, based entirely on the use of overlapping primers. Protocols for executing all of the aforementioned PCR procedures are well known to those skill in the art, and may be found in reference sources such as Gelfand, 1989, PCR Technology, Principles and Applications for DNA Amplification, (Ed.), H. A. Erlich, Stockton Press, N.Y., and Current Protocols In Molecular Biology, Vol. 2, Ch. 15, Eds., Ausubel et al., John Wiley & Sones, 1988.

Sequences containing motifs and multimers isolated using any of the aforementioned approaches may be cloned into convenient bacterial or viral vectors including, but not limited to, plasmids, cosmids, or phages to facilitate any further desired manipulations. Such manipulations of the motif-containing or multimer-containing fragment may include mutagenesis, addition or removal of sequences. For example, useful alterations may include the insertion of other cis-element sequences, sequence motifs, or restriction enzyme sites; conversely the alterations may include the removal of such sequences and sites.

5.2 PA or Iwt Motif Modified Promoters

The PA (SEQ. ID NO:3) and Iwt (SEQ. ID NO:2) motifs of the invention may be used in either monomeric or multimeric form to modify any promoter. A motif or a multimet of the motif, isolated or constructed as described above, can be attached to the 5'-end of a promoter fragment using recombinant DNA methods well know to those skilled in the art. The modified promoter may be a truncated promoter that has been deleted for parts or the whole of sequences 50 basepairs or more 5'upstream of the transcription initiation site; such truncated promoters may or may not retain the AGGA box. Alternatively, the promoter to be modified may be an intact promoter retaining most, if not all, of its upstream enhancer or regulatory sequences.

The recombinant DNA methods for making the PA- or Iwt-modified promoter constructs are well known to those skill in the art (e.g., see Sambrook et al., 1989, Molecular Cloning A Laboratory Manual. Cold Spring Harbor Press). For example, the transcription initiation site of the cloned promoter to be modified can be mapped by methods such as primer extension, RNA/S1 nuclease protection or other equivalent methods. Thereafter, restriction enzyme sites can be constructed at the desired 5' upstream location of the promoter fragment using methods such as in vitro mutagenesis or PCR amplification. Alternatively, such sites may be introduced by resectioning the promoter fragment with Bal31 exonuclease or a 5'-3' exonuclease/mung bean nuclease mix, followed by ligating a oligonucleotide linker containing the desired restriction enzyme sites. Finally, the desired motif or motif multimer can be cloned into the new 5' upstream restriction enzyme sites.

In a preferred embodiment of the present invention, a tetramer of the PA or Iwt motif is attached to the 5'-end of a truncated plant promoter. Such truncated promoters typically comprise of sequences starting at or about the transcription initiation site and extending to no more than 150 bp 5' upstream. These truncated promoters generally are inactive or are only minimally active. Examples of such truncated promoters may include, among others, a "minimal" CaMV 35S promoter whose 5' end terminates at position −46 bp with respect to the transcription initiation site (Skriver et al., Proc. Nat. Acad. Sci. USA 88: 7266–7270); the truncated "−90 35S" promoter in the X-GUS-90 vector (Benfy and Chua, 1989, Science 244: 174–181); a truncated "−101 nos" promoter derived from the nopaline synthase promoter (Aryan et al., 1991, Mol. Gen. Genet. 225: 65–71); and the truncated maize Adh-1 promoter in pADcat 2 (Ellis et al., 1987, EMBO J. 6: 11–16).

In another preferred embodiment of the present invention, the Iwt or PA motif tetramer is attached to the promoter region that is between 50 to 100 basepairs 5' upstream of the transcription initiation site. This location allows the tetramer to strongly exert its regulatory effect on transcription.

In other embodiments of the present invention, it may be desirable to change the number of PA or Iwt motifs attached to a promoter or to vary the distance between a motif-containing sequence and the promoter core. These variations may be used to modulate the regulatory activity of the Iwt or PA motifs. Additional embodiments of the present invention also include promoter constructs containing other types of sequence motifs, in addition to the Iwt or PA motifs. Such additions may be used to expand the expression spectra of the modified promoter.

5.3 Engineering a Gene of Interest Controlled by the Modified Promoters

The PA or Iwt motif-modified promoters of the present invention may be used to direct the expression of any desired RNA product or protein gene product. Useful RNA products include, but are not limited to, "antisense" RNA or ribozymes. Such recombinant construct generally comprise a PA or Iwt motif-modified promoter, as described herein, ligated to the nucleic acid sequence encoding the desired gene product.

Where the desired gene product is a protein, the DNA construct is designed so that the protein coding sequence is ligated in phase with the translational initiation codon downstream of the promoter. Where the promoter fragment is missing a 5' leader sequences, a DNA fragment encoding both the protein and its 5' RNA leader sequence is ligated immediately downstream of the transcription initiation site. Alternatively, an unrelated 5' RNA leader sequence may be used to bridge the promoter and the protein coding sequence. In such instances, the design should be such that protein coding sequence is ligated in phase with the initiation codon present in the leader sequence, or ligated such that no initiation codon interposed between the transcription initiation site and the first methionine codon of the protein.

Further, it may be desirable to include additional DNA sequences in the protein expression constructs. Examples of additional DNA sequences include, but are not limited to, those encoding: a 3' untranslated region; a transcription termination and polyadenylation signal; an intron; a signal peptide (which facilitate the secretion of the protein); or a transit peptide (which targets the protein to a particular cellular compartment such as the nucleus, chloroplast, mitochondria, or vacuole).

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible selectable or screenable marker genes for isolating, identifying or tracking plant cells transformed by these constructs. Selectable markers include, but are not limited to, genes that confer antibiotic resistances, (e.g., resistance to kanamycin or hygromycin) or herbicide resistance (e.g., resistance to sulfonylurea, phosphinothricin, or glyphosate). Screenable markers include, but are not be limited to, genes encoding β-glucuronidase (Jefferson, 1987, Plant Molec Biol. Rep 5: 387–405), luciferase (Ow et al., 1986, Science 234: 856–859), B protein that regulate anthocyanin pigment production (Goff et al., 1990, EMBO J 9: 2517–2522).

In embodiments of the present invention which utilize the *Agrobacterium tumefacien* system for transforming plants (see below), the recombinant constructs may additionally comprise the left and right T-DNA border sequences flanking the DNA sequences to be transformed into the plant cell. The proper design and construction of such T-DNA based transformation vectors are well known to those skill in the art.

5.4 Production of Transgenic Plants and Plant Cells

A recombinant construct containing a gene of interest placed under the control of the Iwt or PA motif-modified promoter, as described herein, is used to transform a plant cell or to genetic engineer plants. The gene of interest may be a heterologous gene or a gene endogenous to the plant. In a preferred embodiement, the *Agrobacterium tumefaciens* is employed to introduce a PA or Iwt-containing recombinant construct into a plant. Such transformation preferably use a binary Agrobacterium T-DNA vector (Bevan, 1984, Nucl. Acid Res. 12: 8711–8721), and the co-cultivation procedure (Horsch et al., 1985, Science 227: 1229–1231). Generally, Agrobacterium is used to transform dicotyledonous plants (Bevan et al. 1982 Ann. Rev. Genet 16: 357–384; Rogers et al., 1986, Methods Enzymol. 118: 627–641). Agrobacterium also may be used to transfer DNA to a wide range of monocotyledonous plants as well (Hernalsteen et al., 1984, EMBO J 3: 3039–3041; Hooykass-Van Slogteren et al., 1984, Nature 311: 763–764; Grimsley et al., 1987, Nature 325: 1677–179; Boulton et al., 1989, Plant Mol. Biol. 12: 31–40.; Gould et al., 1991, Plant Physiol. 95: 426–434).

Alternative methods for introducing PA and Iwt containing constructs into plants or plant cells may also be utilized, particularly if the desired target is a monocotyledonous plant or plant cell. These methods include, but are not limited to, protoplast transformation through calcium-, PEG- or electroporation-mediated uptake of naked DNA (Paszkowski et al., 1984, EMBO J 3: 2717–2722, Potrykus et al. 1985, Molec. Gen. Genet. 199: 169–177; Fromm et al., 1985, Proc. Nat. Acad. Sci. USA 82: 5824–5828; Shimamoto, 1989, Nature 338: 274–276). Other methods for transforming monocotyledonous plants include microinjection, silicon carbide-mediated DNA uptake (Kaeppler et al., 1990, Plant Cell Reporter 9: 415–418), and microprojectile bombardment (Klein et al., 1988, Proc. Nat. Acad. Sci. USA 85: 4305–4309; Gordon-Kamm et al., 1990, Plant Cell 2: 603–618).

The Iwt- or PA-modified gene construct may be introduced into a wide variety of plants and plant cell systems using the transformation methods described above. Preferred transformed plants or plant cells are those of maize, wheat, rice, soybean, tomato, tobacco, carrots, potato, sugar beets, yam, Arabidopsis, or petunia.

Transformed cell or plant may be identified and isolated by selecting or screening for the marker genes present on the transformating DNA. Selection and screening methods in the various plant systems are well known to those skilled in the art. A number of physical and biochemical methods may be used, either independently or together with phenotypic selection or screening, to identify transformants containing the PA and Iwt recombinant constructs. These methods include, but are not limited to: 1) Southern analysis or PCR amplification for detecting and determining the structure of the recombinant DNA insert; 2) Northern blot, S-1 RNase protection, primer-extension or reverse transcriptase-PCR amplification for detecting and examining the RNA transcript; 3) enzymatic assays for detecting the products of the PA or Iwt driven genes, where the gene product is an enzyme or ribozyme; 4) protein gel electrophoresis, western blot techniques, immunoprecipitation, or enzyme-linked immunoassays, where the gene product is a protein. Additional techniques such as in situ hybridization, enzyme staining, and immunostaining, may be used to detect the presence or expression of the recombinant construct in a particular plant organ or tissue. These assays are well known to those skilled in the art.

5.5. Expression of Target Gene Products in Transgenic Plants

The present invention may be advantageously used to direct the expression of a variety of gene products. These gene products include, but are not limited to, proteins, anti-sense RNA and ribozymes.

In particular embodiments of the present invention, by way of illustration, and not by limitation, the Iwt motif-modified promoters which confer developmental-specific expression in seed may be used to express a storage protein such as a phaseolin, a gliadin, a zein, etc. In addition, Iwt motif-modified promoters may be used to express non-plant proteins of exceptional nutritional quality (e.g., casein, ovalbumin) as well as plant proteins engineered to have enhanced nutritional quality (e.g., increased methionine and/or lysine content). The Iwt motif enables the expression of the storage protein to occur during embryogenesis and, thereby, can produce seeds with such enhanced nutritional qualities. The Iwt-modified promoter may also advantageously be used to express insect inhibitory proteins such as the cowpea Bowman-Birk protease inhibitors which have protective effects against herbivorous insects (Hilder et al., 1989, Plant Molec. Biol. 13: 701–710). The embryo-specific expression of such proteins would deter or suppress insect predation of seeds and, thereby, increase seed yields in engineered crop plants.

Other applications of Iwt-modified promoters include controlling the expression of anti-sense, ribozyme or protein genes whose products interfere with basic metabolic or particular embryo-specific functions, and expressing anti-sense or ribozyme molecules designed to remove undesirable traits. The expression of such genes using the Iwt-modified promoters would synchronize and focus the expression of the gene product to the intended target function in the embryo and, thereby, enable specific and efficient alteration of embryo development, structure or metabolism.

PA-modified promoters, which confer root-specific expression, may be advantageously used to express various pest-resistance and disease-resistance genes. Pest resistance genes include the protease inhibitor proteins discussed above, as well as various *Bacillus thuringiensis* endotoxin proteins. PA-modified promoters may also be used to express disease resistance genes, such as, for example, virus coat protein, anti-sense RNA or ribozyme genes for antivirus protection (Gadani et al., 1990, Arch. Virol 115: 1-21); lysozymes and maganins for anti-bacterial protection; or glucanases, osmotins or chitinases for anti-fungal protection. The use of a PA-motif modified promoter would localize and enhance the expression of such a pest-resistance or disease-resistance gene in the roots and, to a lesser extent, in the leaves, thereby, effecting resistance to soil and foliar diseases and pests, such as nematodes and insects. The engineering of such sequences under the control of PA-modified promoters is particularly advantageously applied to root vegetables, including, but not limited to, sugar beets, carrots, turnips, parsnips, etc.

Other applications of PA modified promoters include controlling the expression of anti-sense, ribozyme or protein genes whose products interfere with basic metabolic or particular root or leaf functions. The expression of such genes under the control of a PA-modified promoter would synchronize and focus the expression of these gene products to the intended target functions in the root or leaf and, thereby, enable specific and efficient alterations of development, structure or metabolism of these two organs.

Genes encoding transactivators that bind a PA or Iwt motif and activate transcription may also be genetically engineered into the host plant cell containing the PA or Iwt construct. A preferred transactivator is the TAF-1 protein. Transforming plants with a transactivator genes such as TAF-1 expands the tissue and developmental range of a PA-or Iwt-motif-containing promoter. For example, to achieve light-regulated, leaf-specific expression from a Iwt or PA construct, a rbcS promoter, which has that expression pattern, is used to drive the TAF-1 gene. Since TAF-1 activates PA- or Iwt-motif-containing constructs, TAF-1 factor would act to couple the expression patterns of PA or Iwt motif containing constructs to that of the rbcS promoter. In other embodiments, the same approach is used to expand the plant range of a PA- of Iwt-containing promoter. There, a PA- or Iwt-containing construct may be employed in plants which do not naturally contain transactivators that recognize these motifs by engineering in a cognate transactivator, such as TAF-1, under the control of a promoter that drives expression in the particular plant.

In the working examples described infra, the tobacco transcriptional activator, TAF-1, binds in vitro to two G-box like sequences, PA and Iwt, and its binding affinity for PA is about 70 times higher than that for Iwt (Oeda et al., 1991, EMBO J. 10: 1793-1802). These examples also compare the in vivo expression patterns conferred by these two short sequences with that of a negative control, Imu, a motif I mutant which is unable to bind to the activator in vitro (Oeda et al., 1991, EMBO J. 10: 1793-1802). The results show that PA and Iwt tetramers, which differ only in 2 bp per 10 bp repeat (FIG. 1B) confer strikingly different expression patterns in transgenic tobacco plants. The Imu tetramer, on the other hand, appears to be inactive as a cis-regulatory element because it has no noticeable effect on the expression of the X-GUS-90 promoter. FIG. 6 summarizes in a schematic form the expression patterns obtained with constructs 1 to 4 at different stages of plant development.

PA confers high level expression in roots, low level in leaves, and little or no expression in seeds (FIGS. 3A–3L and 4A–4F) Iwt, on the other hand, confers preferential expression in seeds but in a developmentally-regulated manner. GUS activity appears only at 15 DAF and increases steadily thereafter (FIGS. 3A–3L), and in mature seeds the activity is detected in the entire embryo as well as the endosperm. Although some GUS activity is found in cotyledons of germinating seedlings (FIGS. 4A–4F), this could be due to residual GUS enzyme synthesized during seed development.

The contrasting and almost non-overlapping expression profiles conferred by PA and Iwt strongly suggest that these two cis-regulatory elements interact with different transactivating factors in vivo. These results favor the hypothesis that the transcription activator TAF-1 is the cognate factor for PA for the following two reasons: (1) PA is a high affinity binding site for the activator (Oeda et al., 1991, EMBO J. 10: 1793–1802), and (2) the expression pattern conferred by PA parallels that of TAF-1. Bombardment experiments using a 35S-TAF-1 chimeric construct demonstrated that a transient increase in the expression level of TAF-1 can activate an Iwt-linked transgene in tobacco leaves (Oeda et al., 1991, EMBO J. 10: 1793–1802). Notwithstanding this observation, the example detailed herein demonstrate that Iwt is inactive in root even though this organ expresses TAF-1 at a high level. This result suggests that the high concentration of TAF-1 in roots is still unable to compensate for the low binding affinity of Iwt for this factor.

In comparison to other known seed-specific promoters, the expression pattern conferred by Iwt is of particular interest because it appears to direct expression in both embryos and endosperm. The cis-acting elements studied thus far from seed-specific genes promote expression in specific regions of the seed (cf. Goldberg et al., 1989, Cell 56: 149–160 for a review; Bustos et al., 1991, EMBO J. 10: 1469–1479). Only hex-3 (5' GGACGCGTGGC 3') (SEQ. ID NO:5), a mutant derivative of the hex motif located in the wheat histone H3 promoter (Tabata et al., 1989, EMBO J. 10: 1459–1467), has been shown to confer activity in the embryo, as well as the endosperm of tobacco seeds (Lam & Chua, 1991, J. Biol. Chem. 250: 17131– 17135). Whether Iwt and hex-3 interact with the same or different factors remains to be determined. Iwt (GTACGTGGCG) (SEQ. ID NO:2) shares striking sequence homology (7 out of 9 bp are identical) to the opaque 2 target site (TCTACGTGGA) (SEQ. ID NO:6) in the 5' region of the 22-kD zein gene which is expressed predominantly in maize endosperm (Schmidt et al., 1992, Plant Cell 4: 689–700).

An important consideration for the interpretation of the expression studies described infra is that the constructs were made in the context of the –90 35S promoter (FIG. 1A). As described previously, this promoter confers expression in the radicle of the embryo, the radicle pole of the endosperm and the tips of young and mature roots (Benfey et al., 1989, Science 244: 174–181). By contrast, construct 2 which contains the PA tetramer confers strong expression in the entire root including root hairs (FIGS. 4A and 4B). In addition, the GUS activity in roots containing construct 2 is about 10 times higher than those containing the –90 35S promoter alone (FIG. 2). A 21-bp element, designated as as-1, is responsible for the root expression of the –90 35S promoter (Lam et al., 1989, Proc. Natl. Acad. Sci. USA 86: 7890–7894). It is possible that the strong expression in root, as well as the weak expression in leaf, obtained with construct 2 are generated by a synergistic interaction between PA tetramer and the as-1 element. Similar consideration may also apply to the preferential seed expression seen with construct 3.

To the best of applicant's knowledge, this is the first report that two closely-related plant regulatory sequences such as PA and Iwt can confer completely different expression patterns in transgenic plants. Clearly, these two sequences can be used to direct tissue-specific and developmentally-regulated expression of target genes for basic research as well as biotechnological applications.

6. EXAMPLE: TISSUE-SPECIFIC AND DEVELOPMENTALLY REGULATED EXPRESSION OF TARGET GENE PRODUCTS IN TRANSGENIC TOBACCO

The expression patterns conferred by two G-box related motifs, a perfect palindromic sequence (PA, 5'

GCCACGTGGC 3') (SEQ. ID NO:3) and motif I (Iwt, 5' GTACGTGGCG 3') (SEQ. ID NO:2), were analyzed in transgenic tobacco plants. A mutant version of motif I, Imu, was used as a negative control. PA is not known to be present in the promoters of plant genes, whereas Iwt is a conserved sequence found in ABA-inducible promoters. Previous studies demonstrated that PA and Iwt, but not Imu, can bind to the tobacco transcription activator TAF-1 in vitro, with the PA sequence showing a 70-fold higher affinity as compared to Iwt (Oeda et al., 1991, EMBO J. 10: 1793–1802). Tetramers of PA and Iwt, which differ by only 2 base pairs per 10 base-pair repeat, confer very different tissue-specific and expression patterns in transgenic tobacco plants. PA confers preferential expression in root tissues with a low level of activity in leaves, whereas Iwt directs developmentally regulated expression in seeds beginning from 15 DAF until seed maturation. Imu appears to be inactive as it gives the same expression pattern as the −90 35S promoter control. Norther blot analysis showed that the expression pattern of TAF-1 mRNA is similar to that directed by PA, suggesting that TAF-1 may be involved in the transcriptional regulation of PA.

6.1 Materials and Methods

6.1.1 G-Box-Related Constructs

Construct 1 contains the −90 35S promoter fragment from −90 to +8 CaMV 35S (A domain) fused to the GUS coding sequence (Jefferson et al., 1987, EMBO J. 6: 3901–3907). The 3' end from the pea rbcS-3C gene was placed downstream of the GUS sequence to provide for a polyadenylation signal. This construct was inserted into pMON505 to give the X-GUS-90 vector, which was described in detail elsewhere (Benfey & Chua, 1989, Science 244: 174–181). For construct 2, a head-to-tail tetramer of the perfect palindromic sequence (PA) 5'-GCCACGTGGC-3' (SEQ. ID NO:3) was synthesized with a HindIII site at the 5' end and a XhoI site at the 3' end. The tetramer was then cloned between the HindIII (5') and XhoI (3') sites into a pEMBL12 derivative, sequenced and, then inserted at −90 of X-GUS-90. The same strategy was used to generate constructs 3 and 4 except that the tetramers synthesized corresponded to the wild type motif I (Iwt) 5'-GTACGTGGCG-3' (SEQ. ID NO:2) and the mutant motif I derivative (Imu) 5'-TGACTGTTCT-3' (SEQ. ID NO:4), respectively.

6.1.2 Transgenic Plants

Constructs were mobilized into *Agrobacterium tumefaciens* GV3111SE, and tobacco plants (*Nicotiana tabacum* c.v. SR1) were used for transformation. Shoots were regenerated on medium containing 200 µg/ml kanamycin (Rogers et al., 1986, Methods Enzymol. 118: 627–640). After rooting, transgenic plantelets were transferred to soil and grown in a growth chamber, or maintained, by cuttings, in Plantcons (Tm) containing MS media supplemented with 3% sucrose, 0.7% agar, 100 µg/ml kanamycin, and 500 µg/ml carbenicillin. Primary transformants were allowed to self-fertilize and seeds were collected, sterilized, and germinated on supplemented MS media (see above). Seedlings were maintained at 26° C. under 16 hours of light and 8 hours of dark. Seven to ten independent transgenic plants were analyzed for each construct.

6.1.3 Histochemical Staining

GUS histochemical staining was carried out essentially as described by Jefferson et al., 1987, EMBO J. 6: 3901–3907. The development stages of the seeds used for the assays were determined by tagging flowers of primary transformants when petals had fully expanded (0 DAF). At various intervals hereafter (10 DAF, 15 DAF, and 20 DAF), capsules were removed and 200 µm sections were prepared with a cryotome. Sections were stained by placing them directly into a histochemical substrate solution containing 1 mM 5-bromo-4-chloro-3-indolyl glucuronidase (X-Gluc) and 50 mM sodium phosphate buffer (pH 7.0) on a microscope slide for 12 hours in a humidified chamber at 37° C. Mature seeds were stained as described by Benfey & Chua, 1989, Science 244: 174–181. In order to rule out possible diffusion of the GUS enzyme or dye from one tissue to another during incubation, embryos were removed from endosperms prior to incubation with the substrate. Seven- and 15-days old seedlings were removed from the Petri dishes, and placed directly into the X-Gluc solution and incubated as described for capsule sections (see above). After the incubation, chlorophyll was cleared as described previously (Benfey & Chua, 1989, Science 244: 174–181).

6.1.4 GUS Enzyme Assays

GUS enzyme assays were performed mainly as described by Jefferson et al., 1987, EMBO J. 6: 3901–3907. Extracts were made from leaves and roots of seven week-old plants grown on supplemented MS media (see above), from leaves of seven to ten week-old plants frown in a greenhouse, and from mature seeds. Ten micrograms of protein were incubated with 4-methyl umbelliferyl glucuronide (MUG) solution for 60 minutes at 37° C. The reactions were stoped by adding 2.5 ml of 0.2M sodium carbonate, and fluorescence was measured with a Perkin-Elmer LS5 fluorimeter by using a solution of 100 nM 4-methylumbelliferone (MU) in 0.2M sodium carbonate for calibration.

6.1.5 Northern Analysis

PolyA-plus RNA was extracted from seeds at 20 DAF, and from leaves and roots of seven week-old transgenic tobacco plants grown on supplemented media (see above). RNA was electrophoresed in glyoxal gels and blotted according to standard protocols. Filters were hybridized to the 1.2 Kb labeled EcoRI fragment of TAF-1 cDNA (Oeda et al., 1991, EMBO J. 10: 1793–1802), or to the β-ATPase cDNA (Boutry and Chua, 1985) in a solution of 50% formamide, 5× SSC, 100 µg/ml sonicated salmon sperm DNA, 0.5% SDS, 5× Denhardt's at 42° C. for 20 hours. Filters were washed in 1× SSC, 0.5 SDS at 65° C. for one hour and autoradiographed.

6.2 Results

6.2.1 Engineered Transgenic Plants

To investigate the functional properties of PA and motif I (Iwt), the head-to-tail tetramers comprising tandem copies of these sequences were inserted upstream of the truncated −90 35S promoter in the X-GUS-90 vector (construct 1) to generate constructs 2 and 3, respectively. The X-GUS-90 vector contains the −90 to +8 (A domain) region of the CaMV 35S promoter fused to the β-glucuronidase (GUS) coding sequence, with a 3' fragment of the pea rbcS-3C gene (Benfey & Chua, 1989, Science 244: 174–181). As a negative control, a tetramer of a motif I mutant, TGACTGTTCT (SEQ. ID NO:4), designated as Imu, previously shown to have no binding activity for TAF-1 (Oeda et al., 1991, EMBO J. 10: 1793–1802) was synthesized. The Imu tetramer was also inserted upstream of the truncated 35S promoter in the X-GUS-90 vector to give construct 4. FIG. 1A shows the structures of these chimeric constructs and compares the sequences of the different tetramers used (FIG. 3). The chimeric constructs were transferred to *Agrobacterium tumefaciens*, and tobacco leaf discs were transformed as described in Material and Methods. The expression of the GUS reporter gene was analyzed in primary transformants as well as in their progeny at different developmental stages.

6.2.2 Expression of Target Gene Product in Mature Plants

GUS activity was measured quantitatively in leaves and roots from at least 7 independent transgenic plants for each construct (FIG. 1A). FIG. 2A shows that leaves from plants carrying constructs 3 and 4 expressed a similar level of GUS activity as those from plants containing the X-GUS 90 vector alone (construct 2). By contrast, GUS activity in leaves harboring construct 2 was three to five times higher. The value of GUS activity in the leaves was not affected by the growth conditions of the plants (soil or tissue culture grown plants). In the case of roots, constructs 1 and 4 gave similar GUS expression level whereas constructs 2 and 3 were about ten and two times higher, respectively (FIG. 2B). These results indicate that, in mature plants, PA can confer a high level of expression in roots and, to a lesser degree, in leaves. On the contrary, Iwt and Imu appear to be relatively inactive in these tissues. The 5- to 10-fold higher level of GUS activity conferred by construct 1 (X-GUS-90 vector) in roots as compared to leaves confirms our previous observation that domain A (−90 to +8) of the CaMV 35S promoter shows preferential expression in roots (Benfey et al., 1989, EMBO J. 8: 2195–2202). Because constructs 2, 3, and 4 were all made in the context of the −90 35S promoter, it is possible that the expression patterns obtained with PA reflect the interaction of this sequence with domain A.

6.2.3 Expression of Target Gene Produced During Seed Development

R1 seeds from transgenic plants containing constructs 1 through 4 were analyzed at several stages of development. For this purpose, seeds were harvested at 10, 15, and 20 days after petals had fully expanded (DAF), and also at maturity. Seeds were sectioned, stained for GUS activity, and the stained sections examined by light microscopy as described in Materials and Methods. In the case of mature seeds, the GUS activity in soluble extracts were also determined quantitatively (FIG. 2C).

Seeds that contained PA or Imu did not show any specific GUS staining when compared to control seeds containing the X-GUS-90 vector alone (FIGS. 3A–3C, and FIGS. 3D–3F). In all these three cases, GUS activity was localized, beginning at 15 DAF (not shown), in the radicle of the embryo and in the endosperm cells at the radicle pole (FIGS. 3A–3F). By contrast, Iwt conferred regulated expression in developing seeds. GUS expression was first detected in embryos from seeds at 15 DAF (FIGS. 3G–3I). The expression progressively increased until seed maturity when GUS activity was present in the entire embryo as well as the endosperm (FIGS. 3J–3L). The different seed expression patterns conferred by PA or Imu on one hand, and Iwt on the other hand, were also reflected in quantitative GUS assay of extracts prepared from mature seeds (FIG. 2C). Seeds with Iwt showed about 10 times more GUS activity than seeds with PA or Imu, which gave the same level of activity as seeds from control plants (construct 1).

These results indicate that whereas PA and Imu are inactive in seeds, Iwt can confer specific expression in the embryo and endosperm. However, this expression appears to be developmentally regulated during seed development because GUS activity appears at 15 DAF and subsequently increases until seed maturity. GUS expression in the radicle of the embryos, and in the endosperm cells at the radicle pole, was likely due to the −90 to +8 35S CaMV promoter fragment (A domain) from the X-GUS-90 vector, as already described (Benfey et al., 1989, EMBO J. 8: 2195–2202).

6.2.4 Expression of Target Gene Product in Young Seedlings

R1 seeds from transgenic plants containing constructs 1 through 4 were sterilized and germinated on media as described in Materials and Methods. Seedlings were removed at 7 days (stage of 2 cotyledons) and 15 days (stage of 2 cotyledons and first 2 leaves), and then processed for detection of GUS activity at the cellular level. FIG. 4A shows that 7 day-old seedlings containing PA showed strong GUS activity in roots and weak GUS activity in cotyledons. In seedlings containing Iwt, strong GUS activity was evident in the cotyledons, as well as at the root tips (FIG. 4E). As a negative control, seedlings containing Imu demonstrated identical expression pattern to that of X-GUS-90 control seedlings, i.e. GUS activity was only detected at the root tips (FIG. 4C). At 15 days, seedlings containing PA showed very strong staining in roots, and intermediate staining in the cotyledons and in the first two leaves (FIG. 4B). Expression from Iwt was detected in the cotyledons and at the root tips; however, no GUS activity was visible in the first two leaves (FIG. 4F). In seedlings containing Imu or the X-GUS-90 vector alone (control seedlings), staining was only obtained at the root tips (FIG. 4D).

These results demonstrate that PA and Iwt confer tissue-specific expression in seedlings and, moreover, this expression is developmentally regulated during seed germination. In the case of PA, expression is very strong in roots and, to a lesser degree, in cotyledons and leaves. It should be stressed that this pattern of expression appears only after seed germination. On the other hand, in young seedlings containing the Iwt sequences, expression is detected in cotyledons but, interestingly, not in leaves. In all of the four constructs, the expression detected in the root tip can be attributed to the CaMV 35S A domain in the X-GUS-90 vector (Benfey et al., 1989, EMBO J. 8: 2195–2202).

6.2.5 Expression Pattern of TAF-1 mRNA

A previously characterized cDNA clone encodes a tobacco transcription activator designated as TAF-1 (Oeda et al., 1991, EMBO J. 10: 1793–1802). TAF-1 is a bZIP protein that binds to both Iwt and PA, albeit with striking different affinity, but not to Imu. Because the expression patterns conferred by cis-regulatory elements may reflect the abundance of the transcription factors that interact with them, the expression pattern of TAF-1 mRNA was compared to those conferred by PA and Iwt. In a previous report, TAF-1 mRNA was shown to be 10 to 20 times more abundant in roots than in leaves and stems (Oeda et al., 1991, EMBO J. 10: 1793–1802). The transcriptional activity of Iwt in tobacco seeds (FIGS. 2A–2C and FIGS. 3A–3F) prompted the analysis of the expression of TAF-1 mRNA in this organ. The TAF-1 mRNA level in developing seeds at 20 DAF was inrestiguted because at this stage of seed development, Iwt already conferred a high GUS expression level (see above). FIG. 5A, shows that TAF-1 mRNA was neither detected in developing seeds (20 DAF), nor in leaves. A longer exposure of the autoradiogram only revealed a faint band corresponding in size to that of the TAF-1 mRNA in leaves. As an internal control for the Northern blot analysis, the mRNA coding for the constitutively expressed mitochondrial β-ATPase gene (Boutry & Chua, 1985, EMBO J. 4: 2159–2165) was present at a higher level in seeds as opposed to leaves and roots (FIG. 5B). These results suggested that the expression pattern of TAF-1 mRNA is similar to that conferred by PA (see above). Among the three G-box-binding factors (GBFs) recently cloned from Arabidopsis, GBF3 which shares sequence homology with TAF1 is also highly expressed in roots with little expression in leaves (Schindler et al., 1992, EMBO J. 11: 1261–1273). It would be interesting to see whether GBF3 is also poorly expressed in seeds, as is the case with TAF-1 reported here.

What is claimed is:

1. A modified plant promoter comprising (A) a tetrameric tandem direct repeat of the Iwt motif, GTACGTGGCG, (SEQ ID NO:2) and (B) a promoter or a segment of a promoter, wherein said segment has its 3'-end at the nucleotide corresponding to the transcription initiation site of the homologous gene regulated by said promoter or at any nucleotide that is one to nine basepairs 5'-upstream of the nucleotide corresponding to the transcription initiation site, and said segment has its 5'-end at a nucleotide at least 50 basepairs 5'-upstream of said initiation site; and (A) is coupled to the 5'-end of (B) or is inserted into (B) at a site at least 50 basepairs 5'-upstream of the 3'-end of (B).

2. The modified plant promoter of claim 1, wherein (B) is the –90 CaMV 35 S promoter.

3. A modified plant promoter comprising (A) a tetrameric tandem direct repeat of the PA motif, GCCACGTGGC, (SEQ ID NO:3) and (B) a promoter or a segment of a promoter, wherein said modified plant promoter causes the transcription of an operably linked coding sequence preferentially in the roots or leaves of a plant containing said modified plant promoter and said operably linked coding sequence, said segment has its 3'-end at the nucleotide corresponding to the transcription initiation site of the homologous gene regulated by said promoter or at any nucleotide that is one to nine basepairs 5'-upstream of the nucleotide corresponding to the transcription initiation site, and said segment has its 5'-end at a nucleotide at least 50 basepairs 5'-upstream of said initiation site; and (A) is coupled to the 5'-end of (B) or is inserted into (B) at a site at least 50 basepairs 5'-upstream of the 3'-end of (B).

4. The modified plant promoter of claim 3, wherein (B) is the –90 CaMV 35 S promoter.

5. A genetically engineered DNA molecule comprising the modified plant promoter of claim 1, 2, 3 or 4 operatively linked to the coding sequence of a gene of interest, wherein said modified plant promoter is linked to the 5'-end of said coding sequence and said modified plant promoter regulates the transcription of said coding sequence.

6. A transformed plant cell containing a genetically engineered DNA molecule of claim 5.

7. A transgenic plant containing a genetically engineered DNA molecule of claim 5.

8. A transgenic plant containing a chimeric DNA molecule comprising the modified plant promoter of claim 1 or 2 operatively linked to the coding sequence of a gene of interest, wherein said modified plant promoter is linked to the 5'-end of said coding sequence and said modified plant promoter causes the transcription of said coding sequence in seeds.

9. A transgenic plant containing a chimeric DNA molecule comprising the modified plant promoter of claim 3 or 4 operatively linked to the coding sequence of a gene of interest, wherein said modified plant promoter is linked to the 5'-end of said coding sequence and said modified plant promoter causes the transcription of said coding sequence to occur in roots.

10. The transgenic plant of claim 8, wherein said modified plant promoter causes the transcription of said coding sequence preferentially in the embryos or endosperms of said seeds.

11. A transgenic plant containing a chimeric DNA molecule comprising the modified plant promoter of claim 3 or 4 operatively linked to the coding sequence of a gene of interest, wherein said modified plant promoter is linked to the 5'-end of said coding sequence and said modified plant promoter causes the transcription of said coding sequence to occur in leaves.

* * * * *